(12) United States Patent
Cabalo

(10) Patent No.: US 8,659,753 B1
(45) Date of Patent: Feb. 25, 2014

(54) APPARATUS AND METHOD FOR MEASURING ENERGY IN A LASER BEAM

(75) Inventor: Jerry B. Cabalo, Towson, MD (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 210 days.

(21) Appl. No.: 13/238,518

(22) Filed: Sep. 21, 2011

(51) Int. Cl.
*G01J 1/42* (2006.01)

(52) U.S. Cl.
USPC ............. 356/213; 356/234; 356/235; 374/32

(58) Field of Classification Search
USPC ................ 356/213–226, 121; 374/32, 45
See application file for complete search history.

(56) References Cited

U.S. PATENT DOCUMENTS

| | | | |
|---|---|---|---|
| 3,487,685 A * | 1/1970 | Shifrin | 374/32 |
| 3,746,970 A * | 7/1973 | Van Cleave | 323/238 |
| 4,234,258 A * | 11/1980 | Frosch et al. | 356/437 |
| 4,381,148 A * | 4/1983 | Ulrich et al. | 356/213 |
| 4,606,651 A * | 8/1986 | Anitoff | 374/32 |
| 5,758,969 A * | 6/1998 | Freyaldenhoven | 374/32 |
| 6,970,492 B2 * | 11/2005 | Govorkov et al. | 372/55 |
| 2009/0152250 A1 * | 6/2009 | Chang et al. | 219/121.73 |

\* cited by examiner

*Primary Examiner* — Hoa Pham
(74) *Attorney, Agent, or Firm* — Ulysses John Biffoni

(57) ABSTRACT

A laser energy sensor and methodology for measuring laser energy in a laser beam by photoacoustic means. Laser energy is converted into acoustic energy which is then measured and converted to an energy reading corresponding to the energy of a laser beam.

9 Claims, 4 Drawing Sheets

APPARATUS AND METHOD FOR MEASURING ENERGY IN A LASER BEAM

GOVERNMENT INTEREST

The invention described herein may be manufactured, licensed, and used by or for the U.S. Government.

FIELD OF THE INVENTION

This invention relates to sensors for measuring the energy of a laser beam. More specifically, the invention is a sensor and methodology that employs a photoacoustic effect to measure the energy in a pulsed laser beam.

BACKGROUND OF THE INVENTION

The conventional techniques used to measure energy of a laser beam typically utilize costly technologies such as pyroelectric based sensors. Pyroelectric based sensors rely on the ability of certain materials to generate a temporary voltage when they are heated or cooled. Such sensors are costly to manufacture and can easily command prices of around one thousand dollars per unit.

Prior art thermopiles are based on thermocouples in series which generate a voltage based on the amount of heating caused by absorption of the laser. However, the absorber must be in close contact with the thermopile, and damage to the absorbing surface from the impinging laser will also likely damage the underlying thermopile. Furthermore, replacing the absorbing surface and reintegrating that surface with the thermopile is not easy, so that repair of the sensor is costly.

Prior art pyroelectric detectors are based on the pyroelectric effect, where certain crystals change their voltage based on their temperature. These materials are also susceptible to damage and are also expensive, and the sensor element is not easily replaced.

U.S. Pat. No. 5,758,969 issued to Freyaldenhoven describes an instrument for measuring the energy of optical radiation, particularly laser radiation. The '969 device uses a plurality of radiation absorbing plate-like foraminous elements which are disposed in a tubular housing such that the radiation entering at one end of the housing is successively absorbed by the radiation absorbing elements which are heated thereby. A fan disposed at the other end of the housing moves cooling air through the housing and through the radiation absorbing elements whereby the air is heated. From the temperature increase of the cooling air which is measured by a temperature measuring element, the energy of the optical radiation entering the housing is determined. While the '969 patent issued to Freyaldenhoven has merit it is perhaps a somewhat cumbersome way of determining the energy in a laser beam.

Therefore, a more robust and faster method of measuring the energy in a laser beam is required.

While such technologies as described above have proved useful in measuring and characterizing pulsed laser beams there is a need for less costly sensors.

SUMMARY OF THE INVENTION

A laser energy sensor and methodology for measuring laser energy in a laser beam by acoustic means is provided. Laser energy is converted into acoustic energy which is then measured and converted to an energy reading corresponding to the energy of a laser beam.

DETAILED DESCRIPTION OF THE INVENTION

This invention is directed to sensors for measuring the energy of a pulsed laser beam. More specifically, the invention is a sensor that exploits the photoacoustic effect to measure the energy in a laser beam. The photoacoustic effect occurs when light from a source, such as a laser, is absorbed by a material and the absorbed light is rapidly converted to heat which, is then dissipated to the surroundings. Heat transfer into the gas phase is rapidly converted into the translational motion of gas molecules, which is observed as an increase in pressure. If the light source, such as a laser, is modulated or pulsed at a given frequency then the result is an increase and decrease in pressure at the same frequency as the modulation of the light source. This oscillation of pressure is a sound wave. The intensity, or amplitude, of the pressure waves (sound) is directly proportional to the intensity of the light source and the absorption coefficient of the absorbing material. Thus, the intensity of the light source or laser can be determined from the sound produced. Thus, the invention provides an apparatus and method for measuring energy in a laser beam.

Figure 1:
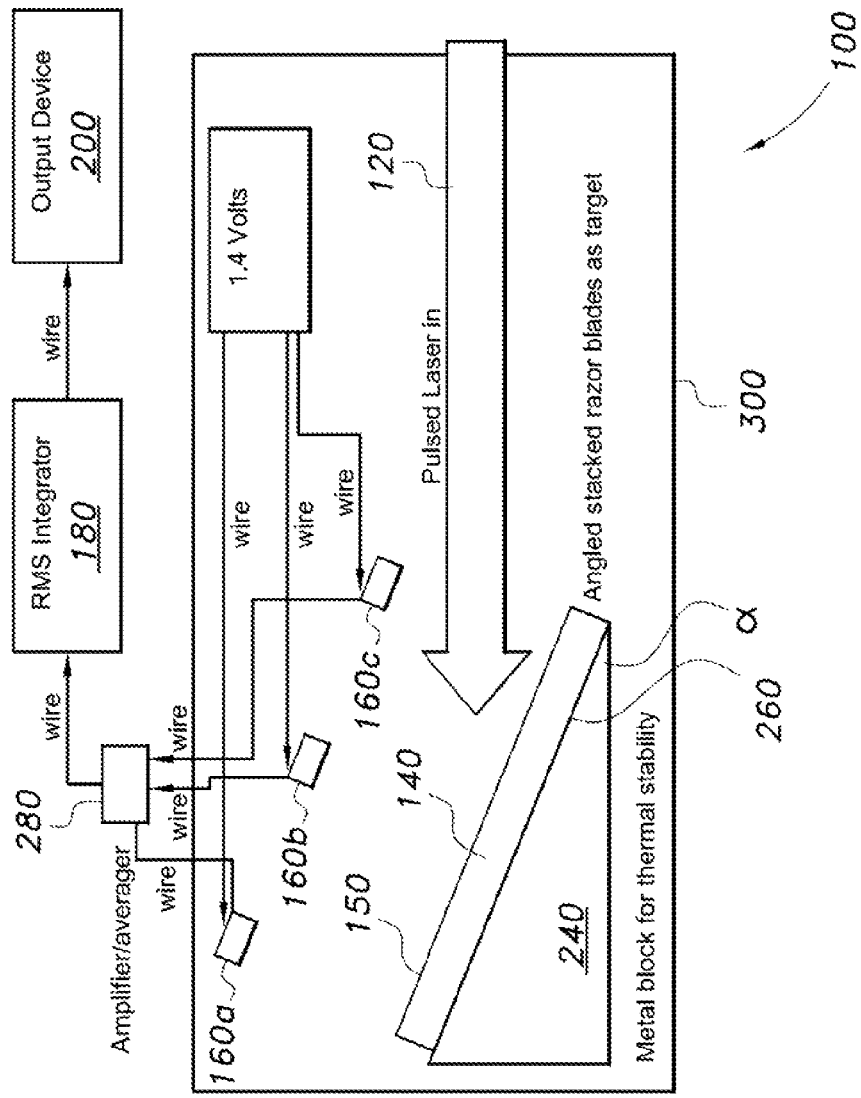
FIG. 1 shows a schematic diagram of a laser energy sensor according to the present invention.

Referring to the Figures, FIG. 1 shows a schematic diagram of a laser energy sensor 100 according to one embodiment of the present invention. A pulsed laser light 120 enters the sensor 100. The pulsed laser 120 is incident on and absorbed by a laser absorber 140. The laser absorber 140 converts at least a portion of the absorbed pulsed laser light into an acoustic signal, i.e., sound energy. The acoustic signal is in proportion to the energy of the pulsed laser light 120.

A plurality of microphones 160 (labeled as "160a", "160b" and "160c") are located proximate to the laser absorber 140. Each microphone detects and converts the sound energy into a voltage signal. A root mean square integrator 180 calculates the root mean square (RMS) voltage value of the voltage signals produced by the microphones 160. The calculated RMS voltage value is proportional to the energy in the pulsed laser light 120. A suitable output device 200 converts the RMS voltage value into a readable format indicative of the energy of the pulsed laser light 120. The output device 200 can be any suitable output device such as, but not limited to, an oscilloscope such as, but not limited to, a Tektronix TDS 5145B digital oscilloscope. The microphones 160 can be replaced with transducers that can detect and convert acoustic noise or vibrations into voltage output signals for input into the root mean square integrator 180.

It should be understood that any suitable material can be used as a laser absorber such as a graphite absorber; however, a high damage threshold laser absorber is preferred so that significant variation in performance of the laser absorber 140 does not occur as absorber material is ablated away. Commercially available laser beam traps can also be used. For example, Thorlabs LB1 beam trap is an acceptable laser absorber. In its most generic embodiment, the laser absorber of the present invention comprises stacked razor blades positioned so that the sharp edges of the blades create narrow openings for receiving the incident laser beam. Unlike a graphite absorber, a stacked razor blade absorber does not suffer from ablation of the absorber surface, which prevents any variation in performance that could occur as absorber material is ablated away. In FIG. 1, the laser absorber 140 is made up of a stack of razor blades located on a metal block 240. The laser absorber 140 defines a laser absorber target surface 150. The razor blades serve as a high damage laser absorber; more specifically, the razor blades maintain an acceptable level of performance by mitigating ablation damage from the pulsed laser source 120. The razor blades slavishly generate sound energy in proportion to the laser energy in the pulsed laser light 120. The razor blades can be aligned in any suitable pattern. For example, the razor blades can be stacked with sharp edges aligned with respect to each other and perpendicular to the surface 150.

Saturation of the sensor surface can occur when laser energy is such that the absorber surface cannot absorb any more light. To limit saturation of the sensor, the absorber is angled at a glancing angle to spread the incoming laser light across the widest possible surface area. Diffusing can also be accomplished using an alumina diffuser, i.e., sintered alumina compressed into a highly porous disc. In FIG. 1, the metal block 240 has a triangular cross-section with a downward facing slope 260 of angle alpha (shown as "α"). The angle alpha should be selected so that the laser beam is distributed across the entire surface 150 of absorber 140. This distributes the energy of the beam 120 across the absorber 140 so that heat is distributed and ablation damage is reduced or eliminated. The laser absorber 140 is located on the slope 260 of the metal block 240 in order to diffuse the incoming beam and avoid saturation. The metal block 240 also acts as a heat sink with respect to the laser absorber 140. More specifically, the metal block 240 provides thermal stability to the laser absorber 140. The metal block 240 can be made out of any suitable metal or metal alloy able to conduct heat away from the laser absorber 140. For example, the metal block 240 can be made out of aluminum or copper.

The microphones 160 can be made up of any suitable microphones. For example, the microphones 160 can be low cost electret microphones that are used in cellular or mobile phones. These microphones are biased with a low voltage, 1.4 Volts is typical. The output of the microphones 160 is directed to an amplifier 280 (current to voltage) and then the signals are averaged. The purpose of averaging is to reduce any variation in the detected signal that depends on the location of the laser beam spot on the face of the absorber 140.

Figure 2:
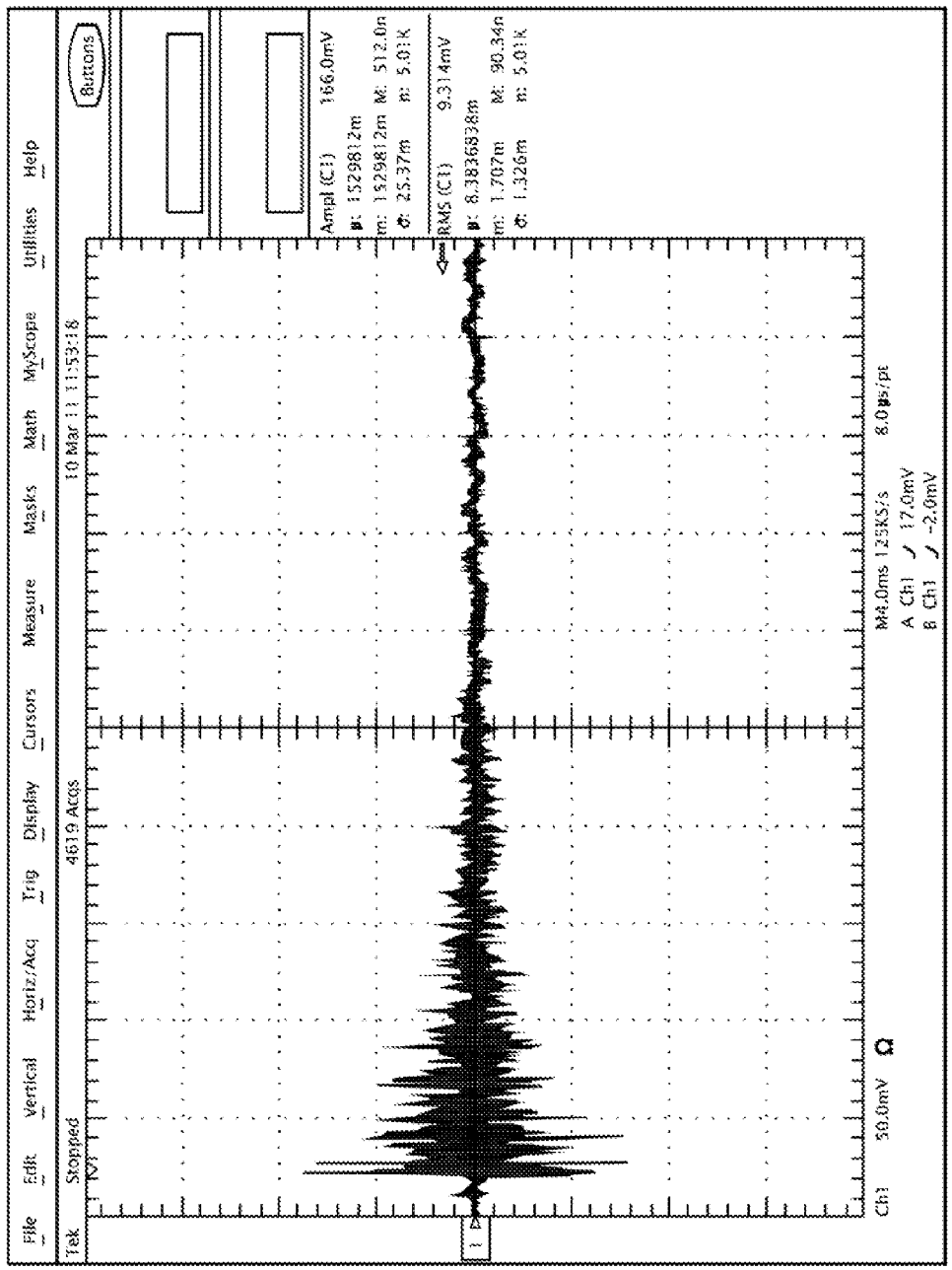
FIG. 2 shows an acoustic signal oscilloscope trace.

FIG. 2 shows an acoustic signal oscilloscope trace of a raw microphone signal obtained from a pulsed Neodymium YAG laser hitting the laser absorber 140 of FIG. 1. Although the laser pulse used in the test is roughly 2.5 nanoseconds in duration, the detected acoustic vibrations persist for about 20 milliseconds. Therefore, to simplify the measurement the root mean square of the microphone voltage is taken over 20 milliseconds.

Figure 3:
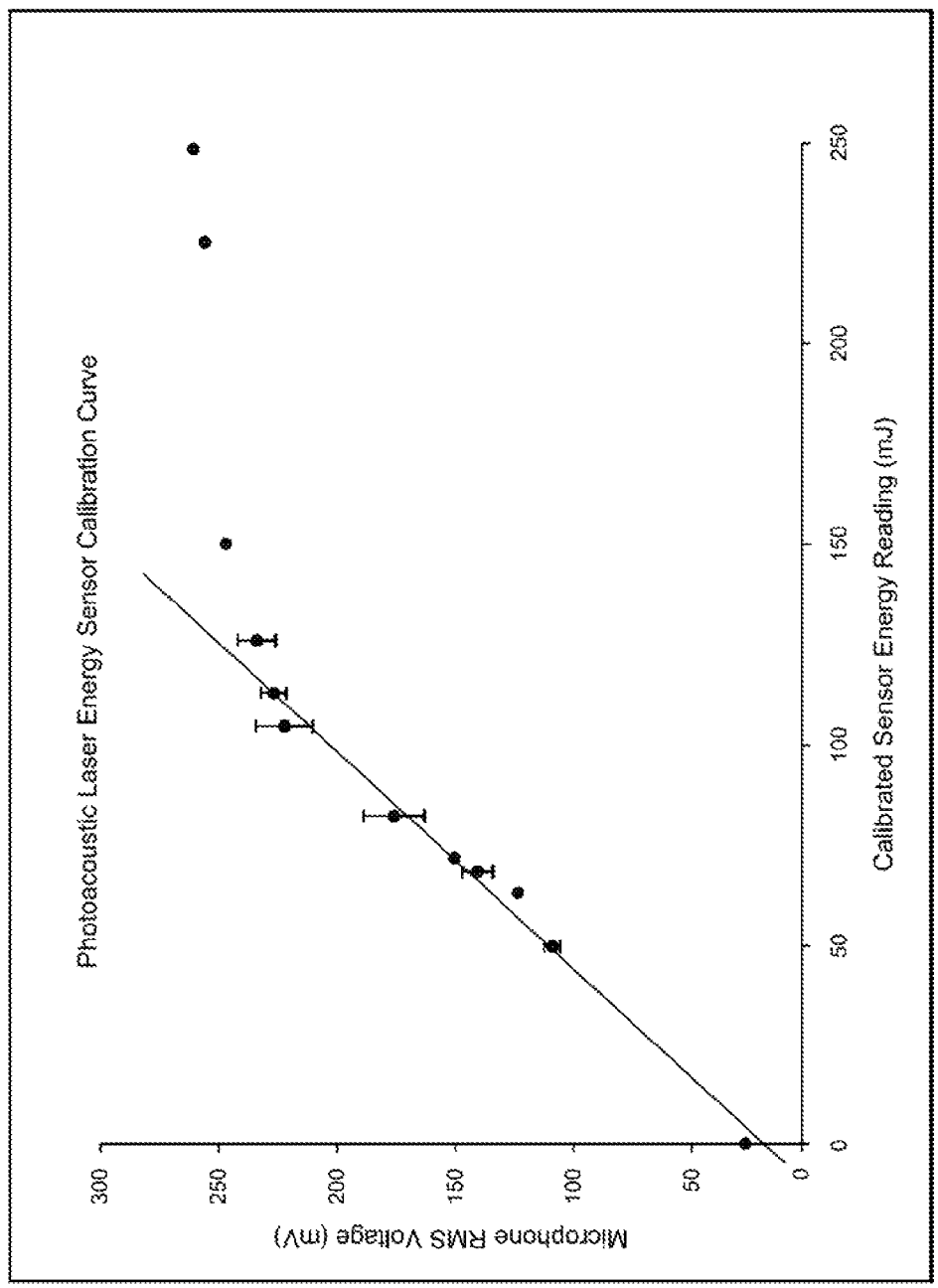
FIG. 3 shows sensor signals as a function of Calibrated Sensor Energy Reading.

FIG. 3 shows sensor signals as a function of Calibrated Sensor Energy Reading (milli-Joules/pulse). The saturation point depends on the absorber material as well as the energy density (laser energy per unit of laser spot area) of the laser spot on the face of the absorber. As shown in FIG. 3, the amount of laser energy is varied over 0-250 milli-Joules per laser pulse. Each laser pulse energy setting is measured with a calibrated pyroelectric sensor with a sintered alumina diffuser. The pyroelectric sensor is then removed so that the pulsed laser beam 120 can strike the absorber target 140 of the photoacoustic sensor 100. The root mean square (RMS) voltage of the acoustic signal is measured with a Tektronix TDS 5145B digital oscilloscope without averaging between laser shots. The dependence of the microphone RMS signal on measured laser pulse energy is shown in FIG. 3.

The measurement plots shown in FIG. 3 show a linear dependence of the microphone RMS voltage on the calibrated laser pulse energy from 0-100 milli-Joules per laser pulse. At about 100 milli-Joules per laser pulse, the response of the sensor configuration tested (FIG. 1), began to saturate, so that no additional microphone response was measured when the laser pulse energy was increased. The absorber 140 can experience saturation, so additional dynamic range can be obtained with a diffuser to spread the laser energy over the absorber 140. The sensor 100 includes a housing 300 for the purpose of reducing scattering of the incoming pulsed laser light 120 that could pose a hazard to the user, as well as protecting the laser absorber target surface 150 from the impingement of dust.

Figure 4:
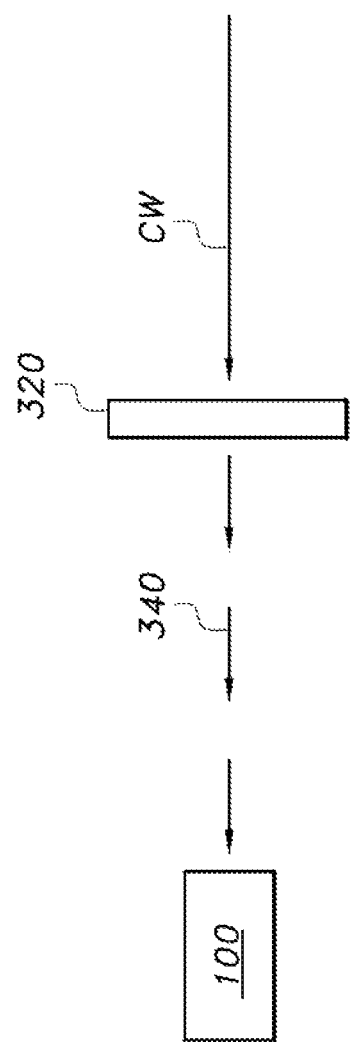
FIG. 4 shows a schematic diagram of a laser energy sensor according to the present invention.

With reference to FIG. 4, the sensor 100 can form part of an apparatus for measuring the energy in a continuous wave (CW) laser beam by placing a chopper wheel 320 in front of the sensor 100. The chopper wheel 320 produces a chopped or pulsed beam 340 that is translated into acoustic sound by sensor 100 and the energy of the beam measured by the sensor 100. Without the chopper wheel 320 a continuous wave laser beam incident on the laser absorber 140 would cause a continuous build up in heat energy, but chopping the laser beam into fragments by chopper wheel 320 results in a cycle of heating and cooling of the laser absorber 140, similar to a pulsed laser, leading to the production of acoustic sound to be picked up by the microphones 160. It is preferred that the laser absorber 140 is a high damage threshold laser absorber as described herein.

The laser energy sensor 100 of the present invention is unique in the field of laser sensors. The sensor 100 potentially has a very low cost and high damage threshold compared to existing laser energy measurement technologies, such as thermopile and pyroelectric technologies.

In another aspect of the invention a method is provided for measuring laser energy in a laser energy beam, comprising the steps of: generating acoustic energy from a laser beam; and converting the acoustic energy into an energy measurement corresponding to the energy in the laser beam.

The invention being thus described, it will be evident that the same may be varied in many ways by a person of skill in the applicable arts. Such variations are not to be regarded as a departure from the spirit and scope of the invention and all such modifications are intended to be included within the scope of the claims.

What is claimed is:

1. A laser energy sensor for measuring energy in a pulsed laser beam, comprising:
   a laser absorber for absorbing and converting pulsed laser light into sound energy in proportion to the energy of the pulsed laser light;
   a metal block having a triangular cross-section and a downward facing slope, wherein said laser absorber is located on said downward facing slope so that the laser absorber is angled with respect to an incoming laser beam so that the laser beam is distributed across the laser absorber maintaining a steady state temperature in said laser absorber;
   a means for converting said sound energy into a plurality of voltage signals;
   a means for converting the plurality of voltage signals into a root mean square voltage value; and
   a means for converting the root mean square voltage value into a readable format indicative of the energy of the pulsed laser light.

2. The laser energy sensor according to claim 1, wherein said metal block comprises a heat conducting material.

3. The laser energy sensor according to claim 2, wherein said metal block comprises a metal or metal alloy.

4. The laser energy sensor according to claim 3, wherein said metal block comprises copper or aluminum.

5. The laser energy sensor according to claim 1, wherein said laser absorber is a high damage threshold laser absorber.

6. The laser energy sensor according to claim 1, wherein said laser absorber is a high damage threshold laser absorber comprising a stack of razor blades.

7. The laser energy sensor according to claim 1, wherein said means for converting sound energy into a plurality of voltage signals comprises a plurality of microphones.

8. The laser energy sensor according to claim 1, wherein said means for converting the plurality of voltage signals into a root mean square voltage value comprises a root mean square integrator.

9. The laser energy sensor according to claim 1, wherein said means for converting said root mean square voltage value into a readable format indicative of the energy of the laser light comprises an oscilloscope.

\* \* \* \* \*